United States Patent
Tien

(10) Patent No.: US 9,066,514 B2
(45) Date of Patent: Jun. 30, 2015

(54) NON-LEVEL MULTILAYER ANTIBACTERIAL SHEET

(76) Inventor: Hsiu-Chuan Tien, Taichung (TW)

( * ) Notice: Subject to any disclaimer, the term of this patent is extended or adjusted under 35 U.S.C. 154(b) by 266 days.

(21) Appl. No.: 13/427,495

(22) Filed: Mar. 22, 2012

(65) Prior Publication Data
US 2013/0251754 A1 Sep. 26, 2013

(51) Int. Cl.
*A61K 9/00* (2006.01)
*A01N 25/34* (2006.01)

(52) U.S. Cl.
CPC ...................................... *A01N 25/34* (2013.01)

(58) Field of Classification Search
CPC ................................ A01N 25/34; A01N 65/00
See application file for complete search history.

(56) References Cited

U.S. PATENT DOCUMENTS

| 6,767,508 B1 * | 7/2004 | Yahiaoui et al. ................. 422/28 |
| 2005/0123590 A1 * | 6/2005 | Burton et al. .................. 424/445 |
| 2005/0181027 A1 * | 8/2005 | Messinger .................... 424/445 |

* cited by examiner

*Primary Examiner* — Hasan Ahmed
(74) *Attorney, Agent, or Firm* — Muncy, Geissler, Olds & Lower, P.C.

(57) ABSTRACT

A non-level multilayer antibacterial sheet comprises a high-fiber substrate, at least one oil absorption film located on the high-fiber substrate and a non-level oil absorption film located at one side of the oil absorption film remote from the high-fiber substrate. The oil absorption film can absorb anti-mildew essential oil. The non-level oil absorption film includes a non-level polyester layer and a second oil absorption layer. The non-level polyester layer and second oil absorption layer form a plurality of housing spaces between them to store the anti-mildew essential oil. Through the oil absorption film and non-level oil absorption film, total amount of absorbed essential oil can be increased to lengthen lifespan of the antibacterial sheet. The housing spaces can store more essential oil and also accelerate evaporation thereof. Thus the anti-mildew essential oil can be dispersed more efficiently to enhance mildew proof effect.

5 Claims, 4 Drawing Sheets

NON-LEVEL MULTILAYER ANTIBACTERIAL SHEET

FIELD OF THE INVENTION

The present invention relates to a liquid absorption sheet and particularly to a non-level multilayer antibacterial sheet.

BACKGROUND OF THE INVENTION

In many damp and warm environments, such as Southeast Asia regions, how to prevent foods or leather goods from being moldy is a common goal of a lot of people. At present a commonly adopted technique to meet this end is to place a chemical agent such as antiseptic, desiccant or deoxidizer into a container to curb or prevent growing of mildews. But used on foods the chemical agent could create ill effects to the health of human body. There is still room for improvement.

Nowadays there are patches and hanging cards absorbed with anti-mildew essential oil on the market. Please refer to FIG. 1, they generally are formed in a sheet structure including a base sheet 1, an upper sheet 2 and an essential oil absorption layer 3 sandwiched therebetween. The essential oil absorption layer 3 aims to absorb anti-mildew essential oil and has one side exposed to the air to evaporate the essential oil. Whether the essential oil is evaporated through the upper sheet 2 or base sheet 1 depends on the material thereof. However, the essential oil absorption layer 3 cannot hold a large amount of the essential oil; after used for a long period of time, the anti-mildew essential oil is almost evaporated to the end, thus replacement has to be done. Usability is lower. In the event that the anti-mildew essential oil is evaporated through the upper sheet 2 or base sheet 1, use duration is even shorter. There is also room for improvement.

SUMMARY OF THE INVENTION

The primary object of the present invention is to solve the problems of the conventional technique that has lower storage capacity of anti-mildew essential oil and faster evaporation to result in frequent replacement.

To achieve the foregoing object, the invention provides a non-level multilayer antibacterial sheet that comprises a high-fiber substrate, at least one oil absorption film located on the high-fiber substrate and a non-level oil absorption film located at one side of the oil absorption film remote from the high-fiber substrate. The oil absorption film includes an impermeable polyester layer and a first oil absorption layer to absorb anti-mildew essential oil. The non-level oil absorption film includes a non-level polyester layer and a second oil absorption layer to absorb the anti-mildew essential oil. The non-level polyester layer and second oil absorption layer form a plurality of housing spaces between them to store the anti-mildew essential oil.

Thus, through the oil absorption film and non-level oil absorption film, absorbed and stored capacity of the anti-mildew essential oil can be increased, thereby increase the lifespan of the non-level multilayer antibacterial sheet. Moreover, the housing spaces formed between the non-level polyester layer and second oil absorption layer can store more anti-mildew essential oil and increase evaporation speed thereof, hence can improve dispersion of the anti-mildew essential oil and mildew proof effect.

The foregoing, as well as additional objects, features and advantages of the invention will be more readily apparent from the following detailed description, which proceeds with reference to the accompanying drawings.

DETAILED DESCRIPTION OF THE PREFERRED EMBODIMENTS

Figure 1:
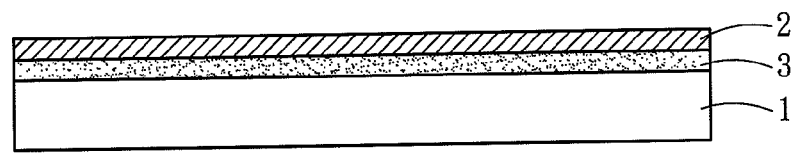
FIG. 1 is a cross section of a conventional technique.
Figure 2A:
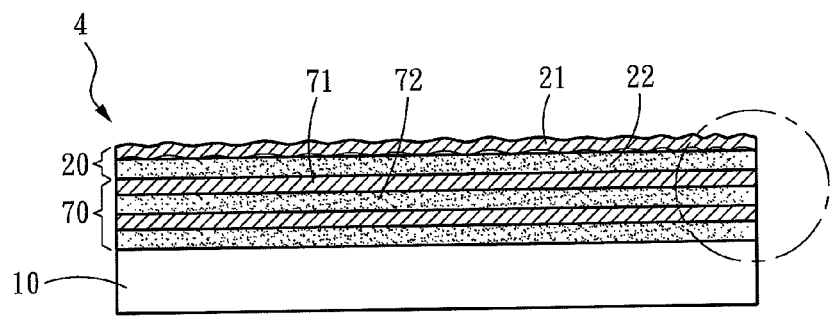
FIG. 2A is a schematic cross section of a first embodiment of the invention.
Figure 2B:
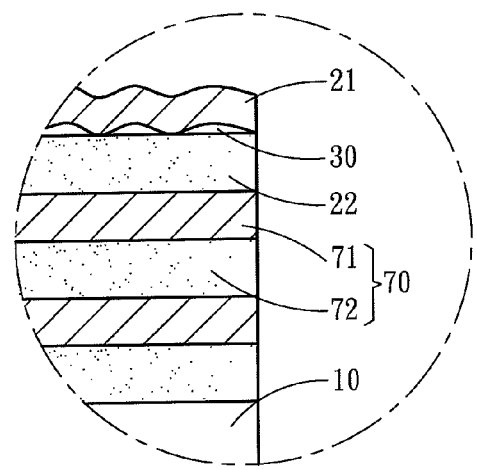
FIG. 2B is a fragmentary enlarged cross section of the first embodiment of the invention.

Please refer to FIGS. 2A and 2B for a first embodiment of the invention. The invention aims to provide a non-level multilayer antibacterial sheet 4 that comprises a high-fiber substrate 10, at least one oil absorption film 70 located on the high-fiber substrate 10 and a non-level oil absorption film 20 located at one side of the oil absorption film 70 remote from the high-fiber substrate 10. The oil absorption film 70 includes an impermeable polyester layer 71 and a first oil absorption layer 72 to absorb anti-mildew essential oil. In this embodiment, the first oil absorption layer 72 is adjacent to the high-fiber substrate 10, while the impermeable polyester layer 71 is located at one side of the first oil absorption layer 72 remote from the high-fiber substrate 10. The oil absorption film 70 can be formed in multiple sets stacked over each other. The non-level oil absorption film 20 includes a non-level polyester layer 21 and a second oil absorption layer 22 to absorb the anti-mildew essential oil. The non-level polyester layer 21 and second oil absorption layer 22 form a plurality of housing spaces 30 between them to store the anti-mildew essential oil. It is to be noted that the non-level oil absorption film 20 can be made in a corrugated manner through a manufacturing process during bonding various films, or via a special embossing process. The first oil absorption layer 72 and second oil absorption layer 72 can be made of non-plastic adhesive. After the oil absorption layer 70, non-level oil absorption film 20 and high-fiber substrate 10 are bonded together, the anti-mildew essential oil is absorbed by the high-fiber substrate 10, oil absorption film 70 and non-level oil absorption film 20 via a vaporization process. This is a regular essential oil absorption process known in the art, thus details are omitted herein.

Figure 3:
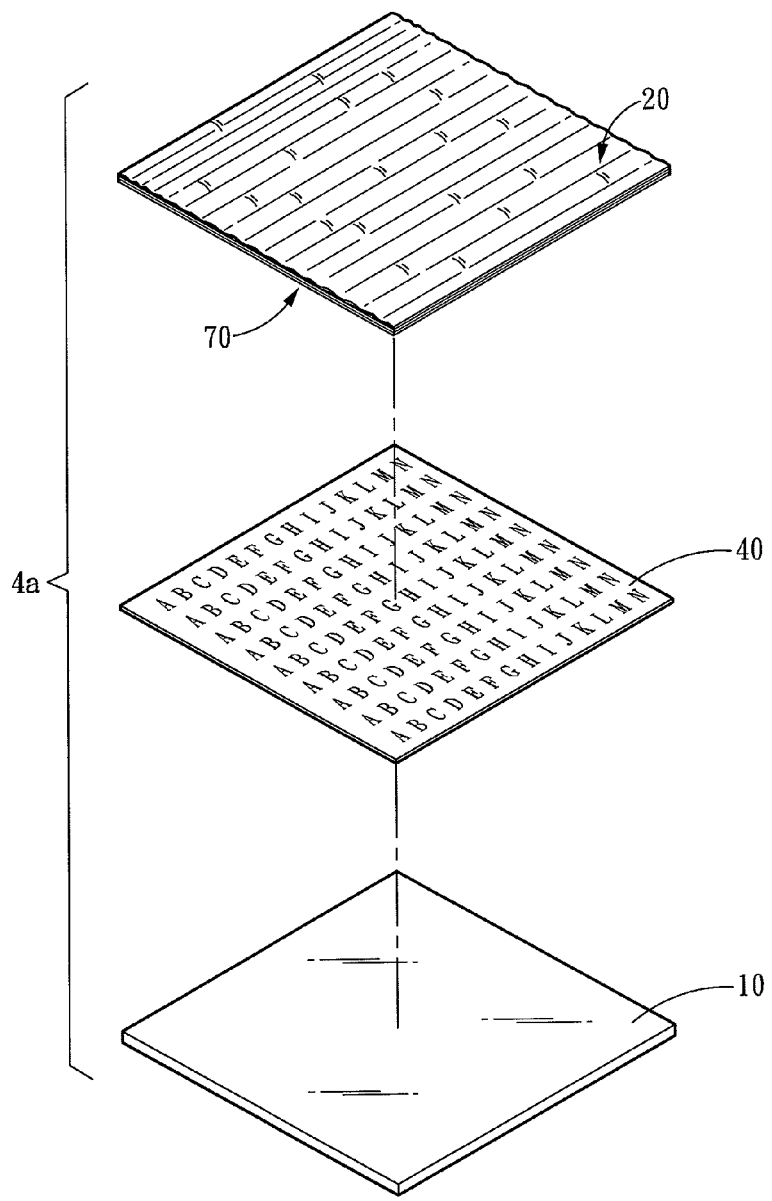
FIG. 3 is an exploded view of a second embodiment of the invention.

Please refer to FIG. 3 for a second embodiment of the invention. In order to form a desired pattern on the non-level multilayer antibacterial sheet 4a to improve aesthetic appeal and mark use instructions and cautionary messages such as inedible remarks as well, an ink layer 40 may be provided between the high-fiber substrate 10 and oil absorption film 70. In this embodiment, the ink layer 40 is made of coated paper. Through the ink layer 40 the non-level multilayer antibacterial sheet 4a can be formed with text or graphic display function.

Figure 4:
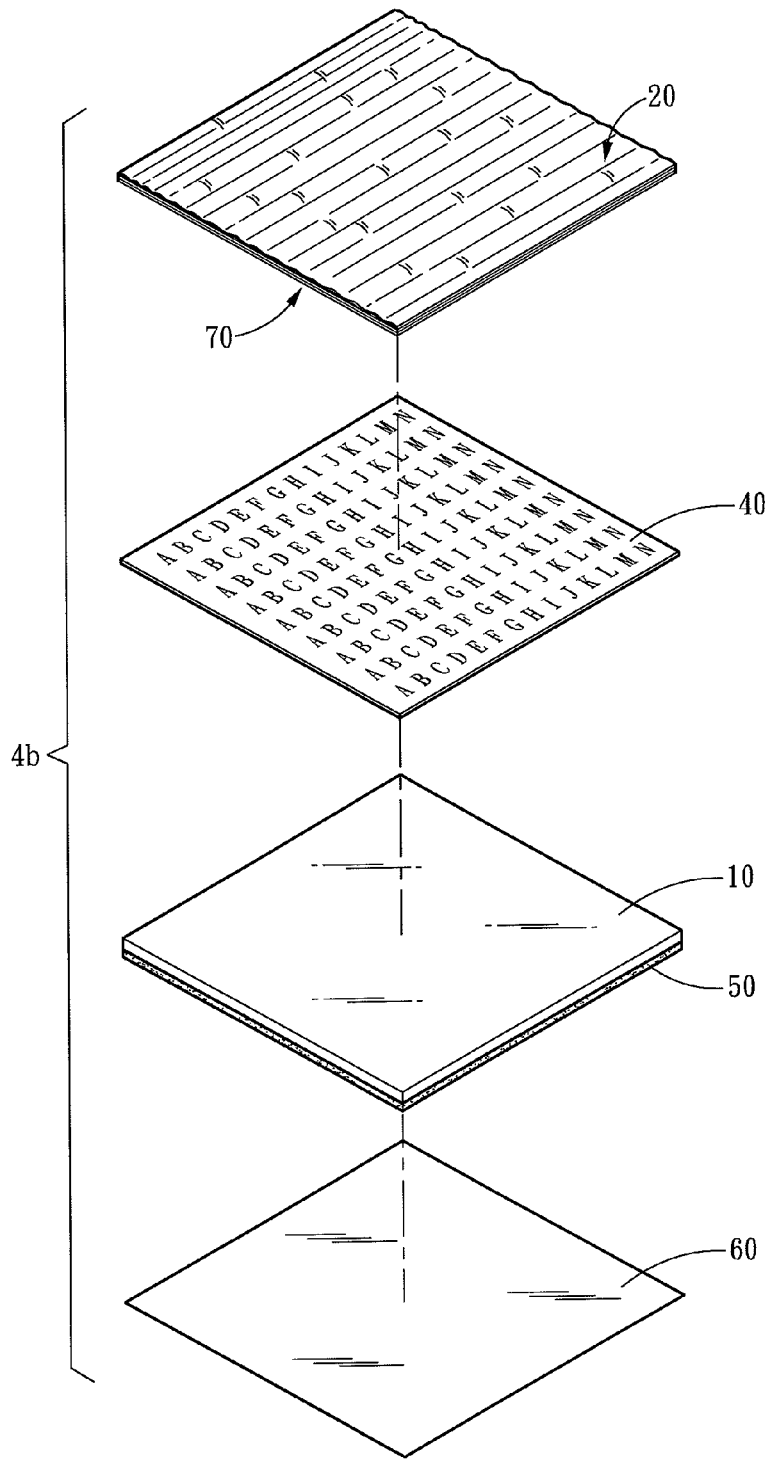
FIG. 4 is an exploded view of a third embodiment of the invention.

Please refer to FIG. 4 for a third embodiment of the invention. The non-level multilayer antibacterial sheet 4b can also be formed with bonding function. To meet this end, a bonding layer 50 is formed at one side of the high-fiber substrate 10 remote from the oil absorption film 70, and a release paper 60 is provided and bonded to one side of the bonding layer 50 remote from the high-fiber substrate 10.

As a conclusion, compared with the conventional technique, the invention provides features as follow:

1. Through multiple sets of the oil absorption films stacked over one another, more anti-mildew essential oil can be stored, hence evaporation period of the anti-mildew essential oil increases and total lifespan enhances.

2. The housing spaces formed between the non-level polyester layer and second oil absorption layer can increase storing capacity of the anti-mildew essential oil, and also increase contact area with the air, hence can accelerate evaporation of the anti-mildew essential oil and enhance dispersion thereof to improve mildew proof effect. It provides significant improvements over the conventional technique.

While the preferred embodiments of the invention have been set forth for the purpose of disclosure, they are not the limitations of the invention, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A non-level multilayer antibacterial sheet, comprising:
a high-fiber substrate containing anti-mildew essential oil;
at least one oil absorption film located on the high-fiber substrate and including an impermeable polyester layer and a first oil absorption layer containing anti-mildew essential oil, said first oil absorption layer being adjacent to the high-fiber substrate, said impermeable polyester layer being located at one side of the first oil absorption layer remote from the high-fiber substrate, and said impermeable polyester layer and said first oil absorption layer being in direct contact with no housing spaces; and
a non-level oil absorption film which is corrugated and located at one side of the oil absorption film remote from the high-fiber substrate and includes a second oil absorption layer connected to the at least one oil absorption film containing the anti-mildew essential oil, a non-level polyester layer located at one side of the second oil absorption layer remote from the at least one oil absorption film, and a plurality of housing spaces formed between the non-level polyester layer and the second oil absorption layer to store the anti-mildew essential oil and accelerate evaporation of the anti-mildew essential oil;
wherein the first oil absorption layer and the second oil absorption layer are made of non-plastic adhesive.

2. The non-level multilayer antibacterial sheet of claim 1, wherein the oil absorption film includes multiple sets stacked over each other, with adjacent sets being in direct contact with no housing spaces.

3. The non-level multilayer antibacterial sheet of claim 1 further including a bonding layer located at one side of the high-fiber substrate remote from the oil absorption film and a release paper adhering to one side of the bonding layer remote from the high-fiber substrate.

4. The non-level multilayer antibacterial sheet of claim 1 further including an ink layer between the high-fiber substrate and the non-level oil absorption film.

5. The non-level multilayer antibacterial sheet of claim 4, wherein the ink layer is made of coated paper.

\* \* \* \* \*